United States Patent
Van Rossum et al.

(10) Patent No.: US 12,215,073 B2
(45) Date of Patent: Feb. 4, 2025

(54) INTEGRATED ETHYLENE PRODUCTION PROCESS

(71) Applicant: SHELL OIL COMPANY, Houston, TX (US)

(72) Inventors: Guus Van Rossum, Amsterdam (NL); Ronald Jan Schoonebeek, Amsterdam (NL); Ivana Daniela Esposito Cassibba, Amsterdam (NL); Alouisius Nicolaas Renée Bos, Amsterdam (NL)

(73) Assignee: SHELL USA, INC., Houston, TX (US)

(*) Notice: Subject to any disclaimer, the term of this patent is extended or adjusted under 35 U.S.C. 154(b) by 147 days.

(21) Appl. No.: 18/006,159

(22) PCT Filed: Aug. 3, 2021

(86) PCT No.: PCT/EP2021/071637
§ 371 (c)(1),
(2) Date: Jan. 20, 2023

(87) PCT Pub. No.: WO2022/029108
PCT Pub. Date: Feb. 10, 2022

(65) Prior Publication Data
US 2023/0295060 A1    Sep. 21, 2023

(30) Foreign Application Priority Data

Aug. 3, 2020 (EP) .................................... 20189089

(51) Int. Cl.
*B01D 53/62* (2006.01)
*B01D 53/26* (2006.01)
(Continued)

(52) U.S. Cl.
CPC ............ *C07C 4/025* (2013.01); *B01D 53/265* (2013.01); *B01D 53/62* (2013.01); *B01D 53/78* (2013.01);
(Continued)

(58) Field of Classification Search
None
See application file for complete search history.

(56) References Cited

U.S. PATENT DOCUMENTS 3,829,521 A    8/1974  Green
4,250,346 A    2/1981  Young et al.
(Continued)

FOREIGN PATENT DOCUMENTS

CA    1262556 A    10/1989
CN    1208669 A    2/1999
(Continued)

OTHER PUBLICATIONS

Notice of Allowance Received for Kazakhstan Application No. 2023/0148.1, Mailed on May 31, 2024, 19 pages (09 Pages of English Translation and 10 Pages of Official Copy).
(Continued)

*Primary Examiner* — Tam M Nguyen
(74) *Attorney, Agent, or Firm* — SHELL USA, INC.

(57) ABSTRACT

The invention relates to a process for the production of ethylene in an integrated configuration comprising (i) a steam cracker configuration which comprises a steam cracker unit, a water condensation unit and a carbon dioxide removal unit and (ii) an oxidative dehydrogenation (ODH) configuration which comprises an ODH unit and a water condensation unit, wherein an effluent coming from the ODH configuration, which effluent comprises unconverted ethane and ethylene, is fed to the steam cracker configuration at a position which is downstream of the steam cracker unit, and wherein unconverted oxygen, carbon monoxide and acetylene are removed from at least a portion of the stream coming from the ODH unit by oxidation of carbon monoxide and acetylene into carbon dioxide in an oxidation unit which is located at a position (a) which is downstream of the ODH unit, and (b) which is downstream of the steam (Continued)

cracker unit and upstream of the carbon dioxide removal unit of the steam cracker configuration.

9 Claims, 3 Drawing Sheets

(51) Int. Cl.
  *B01D 53/78* (2006.01)
  *C07C 4/02* (2006.01)
(52) U.S. Cl.
  CPC .. *B01D 2251/304* (2013.01); *B01D 2251/604* (2013.01); *B01D 2252/204* (2013.01); *B01D 2257/504* (2013.01); *B01D 2257/80* (2013.01)

(56) References Cited

U.S. PATENT DOCUMENTS

| | | | |
|---|---|---|---|
| 4,365,271 A | 12/1982 | Blom | |
| 4,524,236 A | 6/1985 | McCain | |
| 4,596,787 A | 6/1986 | Manyik et al. | |
| 4,720,293 A | 1/1988 | Rowles et al. | |
| 5,430,181 A | 7/1995 | Arpentinier et al. | |
| 5,534,650 A | 7/1996 | Ushikubo et al. | |
| 6,518,476 B1 | 2/2003 | Culp et al. | |
| 7,015,355 B2 | 3/2006 | Zeyss et al. | |
| 7,091,377 B2 | 8/2006 | Borgmeier et al. | |
| 7,319,179 B2 | 1/2008 | Lopez Nieto et al. | |
| 7,553,888 B2 | 6/2009 | Greenwood et al. | |
| 8,013,196 B2 | 9/2011 | Mamedov et al. | |
| 8,080,697 B2 | 12/2011 | Lin et al. | |
| 8,242,048 B2 | 8/2012 | Rosen | |
| 8,273,680 B2 | 9/2012 | Raichle et al. | |
| 8,524,927 B2 | 9/2013 | Mazanec et al. | |
| 8,846,996 B2 | 9/2014 | Kustov et al. | |
| 8,969,602 B2 | 3/2015 | Verhaak | |
| 9,067,901 B2 | 6/2015 | Verhaak et al. | |
| 9,187,647 B2 | 11/2015 | Greenwood et al. | |
| 9,249,317 B2 | 2/2016 | Greenwood et al. | |
| 9,404,062 B2 | 8/2016 | Yaguchi et al. | |
| 9,676,695 B2 | 6/2017 | Nunley et al. | |
| 9,738,585 B2 | 8/2017 | Karime | |
| 9,963,412 B2 | 5/2018 | Bos et al. | |
| 9,993,798 B2 | 6/2018 | Simanzhenkov et al. | |
| 10,329,222 B2 | 6/2019 | Bos et al. | |
| 10,357,754 B2 | 7/2019 | Simanzhenkov et al. | |
| 10,472,583 B2 | 11/2019 | Utaka | |
| 11,041,132 B2 | 6/2021 | Oki et al. | |
| 11,052,383 B2 | 7/2021 | Weller et al. | |
| 11,078,134 B2 | 8/2021 | Mitkidis et al. | |
| 2004/0097600 A1 | 5/2004 | Greenwood et al. | |
| 2004/0147393 A1 | 7/2004 | Hibst et al. | |
| 2005/0107650 A1 | 5/2005 | Sumner | |
| 2007/0111908 A1 | 5/2007 | Lam et al. | |
| 2007/0112236 A1 | 5/2007 | Bridges et al. | |
| 2009/0281345 A1 | 11/2009 | Matusz | |
| 2010/0069659 A1 | 3/2010 | Raichle et al. | |
| 2010/0069660 A1 | 3/2010 | Raichle et al. | |
| 2010/0222623 A1 | 9/2010 | Ryan | |
| 2010/0256432 A1 | 10/2010 | Arnold et al. | |
| 2011/0212384 A1 | 9/2011 | Luo et al. | |
| 2012/0190900 A1 | 7/2012 | Weston et al. | |
| 2013/0197290 A1 | 8/2013 | Domokos et al. | |
| 2014/0113848 A1 | 4/2014 | Miyamoto et al. | |
| 2014/0114109 A1 | 4/2014 | Sanchez Valente et al. | |
| 2014/0209506 A1 | 7/2014 | Domokos et al. | |
| 2014/0342958 A1 | 11/2014 | Kubo et al. | |
| 2015/0014183 A1 | 1/2015 | Akay et al. | |
| 2015/0119622 A1 | 4/2015 | De Rooij et al. | |
| 2015/0133686 A1 | 5/2015 | Macht et al. | |
| 2015/0202602 A1 | 7/2015 | Shu et al. | |
| 2015/0275130 A1 | 10/2015 | Willers et al. | |
| 2016/0237003 A1 | 8/2016 | Mammadov et al. | |
| 2016/0237005 A1 | 8/2016 | Kumar et al. | |
| 2016/0326070 A1 | 11/2016 | Winkler et al. | |
| 2017/0226030 A1 | 8/2017 | Li et al. | |
| 2019/0194091 A1 | 6/2019 | Mitkidis et al. | |
| 2019/0203148 A1 | 7/2019 | Scholler et al. | |
| 2020/0263106 A1 | 8/2020 | Ueda et al. | |
| 2022/0153661 A1* | 5/2022 | Fritz | C07C 2/84 |
| 2023/0028068 A1* | 1/2023 | Kim | C07C 5/48 |
| 2023/0338911 A1* | 10/2023 | Simanzhenkov | C07C 7/11 |
| 2024/0149253 A1* | 5/2024 | Gao | B01J 37/088 |

FOREIGN PATENT DOCUMENTS

| | | |
|---|---|---|
| CN | 1269258 A | 10/2000 |
| CN | 1269341 A | 10/2000 |
| CN | 101045214 A | 10/2007 |
| CN | 103086821 A | 5/2013 |
| CN | 103121891 A | 5/2013 |
| CN | 103965002 A | 8/2014 |
| CN | 103551148 B | 8/2015 |
| EP | 0261264 B1 | 8/1991 |
| JP | 2014210844 A | 11/2014 |
| JP | 2014224070 A | 12/2014 |
| WO | 2004035474 A1 | 4/2004 |
| WO | 2010053459 A1 | 5/2010 |

OTHER PUBLICATIONS

International Search Report and Written Opinion Received for PCT Patent Application No. PCT/EP2021/071637, Mailed on Oct. 28, 2021, 9 Pages.
Gao et al.,"A Molten Carbonate Shell Modified Perovskite Redox Catalyst for Anaerobic Oxidative Dehydrogenation of Ethane", Science Advances, vol. 6, Apr. 24, 2020, 11 Pages.
Zimmermann et al., "Ethylene", Ullmann's Encyclopedia of Industrial Chemistry, 2012, vol. 13, pp. 465-529.
Office Action Received for Brazilian Application No. BR112019001830-1, Mailed on May 3, 2022, 13 Pages (5 Pages of English Translation and 8 Pages of Official Copy).
International Search Report and Written Opinion received for PCT Patent Application No. PCT/EP2017/069266, Mailed on Sep. 28, 2017, pp. 12.
Roussel et al., Oxidation of Ethane to Ethylene and Acetic Acid by Movnbo Catalysts, Catalysis Today, 2005, vol. 99, pp. 77-87.
Office Action Received for U.S. Appl. No. 15/770,691, Mailed on Feb. 2, 2022, 11 Pages (11 Pages of Official Copy).
Office Action Received for IN Application No. 202047017465, Mailed on Oct. 25, 2021, 07 Pages (7 Pages of Official Copy).
Valente et al., "Chemical, Structural and Morphological Changes of Movtenb Catalyst During Oxidative Dehydrogenation of Ethane", ACS Catalysis, vol. 4, Issue No. 5, pp. 26.
Yang et al., "Review on the Methods of Separation and Recovery of Acetic Acid From Aqueous Solution", Environmental Protection of Chemical Industry, vol. 15, Issue No. 2, Apr. 30, 1995, pp. 6 (English Abstract Only).
Ya et al., "Structure and Catalytic Properties Deposited Oxide-molybdenum, Oxide-vanadium and Chromium Oxide Dehydrogenation Catalysts Hydrocarbons", Bulletin of Kuzbass University, 2007, pp. 73-93 (English Abstract Only).
Zhang et al., "Progress in the Study of Ethane Dehydrogenation Catalyst", Chemical Industry and Engineering Progress, vol. 39, Issue No. 6, Mar. 16, 2020, pp. 2390-2398 (English abstract only).
Nguyen et al., "Optimizing the Efficiency of Movtenbo Catalysts for Ethane Oxidative Dehydrogenation to Ethylene", Catalysis Communications, vol. 21, May 2012, pp. 22-26.
Process Economics Program Report 37C, Acetic Acid, Dec. 2001, 174 pages.
Pyrz et al., Supporting information, 2 pages.
Lobera et al., "High Ethylene Production through Oxidative Dehydrogenation of Ethane Membrane Reactors Based on Fast Oxygen-Ion Conductors", ChemCatChem, 2011, vol. 3, Issue No. 9, pp. 1503-1508.
International Search Report and Written Opinion received for PCT Patent Application No. PCT/EP2016/071948, mailed on Nov. 21, 2016, 8 pages.

(56) References Cited

OTHER PUBLICATIONS

International Search Report and Written Opinion received for PCT Patent Application No. PCT/EP2016/075591, mailed on Jan. 13, 2017, 12 pages.
Baca et al., "Bulk Oxidation State of the Different Cationic Elements in the Movte(Sb)nbo Catalysts for Oxidation or Ammoxidation of Propane", Applied Catalysis a: General, vol. 279, Issue No. 1-2, Jan. 28, 2005, pp. 67-77.
Pyrz et al., "Atomic-level Imaging of Mo—v—o Complex Oxide Phase Intergrowth, Grain Boundaries, and Defects Using Haadf-stem", Pnas, Apr. 6, 2010, vol. 107, No. 14, pp. 6152-6157.
Novakova et al.,"Propane Oxidation on Mo—V—Sb—Nb Mixed-Oxide Catalysts: 1. Kinetic and Mechanistic Studies", Journal of Catalysis, vol. 211, Issue No. 1, Oct. 1, 2002, pp. 226-234.
Roussel et al.,"Movo-based Catalysts for the Oxidation of Ethane to Ethylene and Acetic Acid: Influence of Niobium and/or Palladium on Physicochemical and Catalytic Properties", Applied Catalysis a General, vol. 308, 2006, pp. 62-74.
"Levasil and Bindzil Colloidal Silica Dispersions", for the Adhesive Industry—Uses and Benefits, Akzonobel, 2011, 6 Pages.
Bindzil CC in Waterborne Coating Applications Silane Modified Colloidal Silica—Uses and Benefits, Akzonobel, 2011, 6 Pages.
International Search Report and Written Opinion Received for PCT Application No. PCT/EP2016/075593, Mailed on Jan. 26, 2017, 8 Pages.
Phase-pure Mo—V—Te—Nb—O M1 Catalysts for Propane Oxidation, 1 Page.

\* cited by examiner

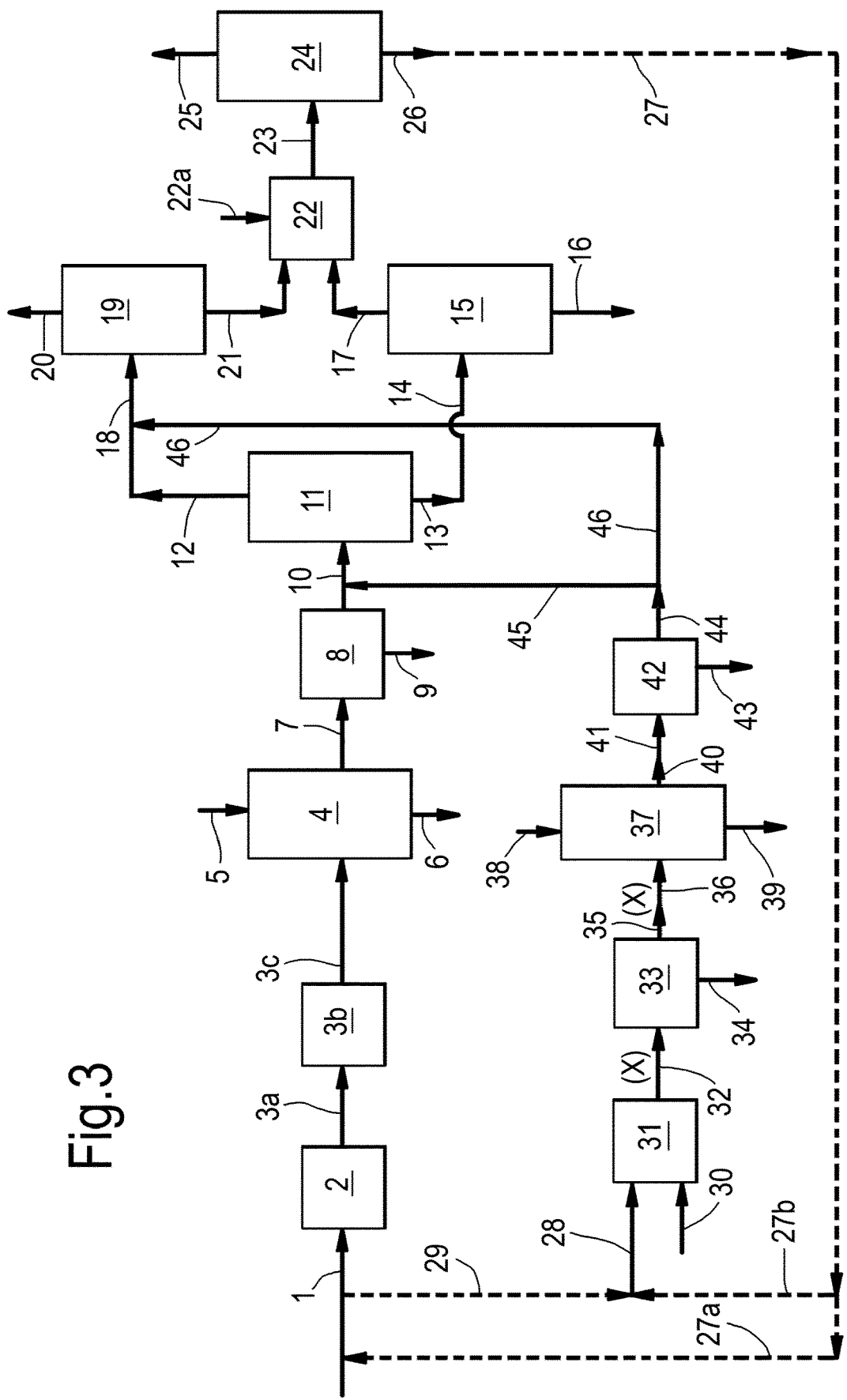

INTEGRATED ETHYLENE PRODUCTION PROCESS

CROSS REFERENCE TO RELATED APPLICATIONS

This is a National stage application of International Application No. PCT/EP2021/071637, filed 3 Aug. 2021, which claims priority of EP Application No. 20189089.4, filed 3 Aug. 2020 which is incorporated herein by reference in its entirety.

FIELD OF THE INVENTION

The present invention relates to an integrated process for the production of ethylene.

BACKGROUND OF THE INVENTION

It is known to produce ethylene by steam cracking a feed stream comprising saturated hydrocarbons, which may include one or more of ethane, propane, butane, liquefied petroleum gas (LPG), naphtha, hydrowax and recycled waste plastics oil, under the influence of heat into a product stream comprising ethylene and hydrogen. Before any subsequent step wherein the ethylene is further converted into useful chemical intermediates, the ethylene containing product stream has to be purified. In addition to ethylene and hydrogen, a steam cracker product stream may also contain acetylene and unconverted ethane. Further, said product stream may contain some carbon monoxide and carbon dioxide as impurities. Carbon dioxide may be produced in the presence of oxygen (resulting from some small air ingress into the steam cracker unit) and/or in water-shift reactions of hydrocarbons. Further, carbon monoxide and carbon dioxide may be present as contaminants in the feed. Still further, said product stream may contain methane and C3+ hydrocarbons which impurities may be formed during steam cracking of ethane which is generally a non-catalytic, non-selective conversion process. The latter impurities may also originate from the ethane feed stream. Components other than ethylene need to be removed from the product stream as they may interfere in any subsequent step wherein ethylene is further converted. Examples of said C3+ hydrocarbons include propylene and butylenes.

Generally, carbon dioxide is removed from the steam cracker product stream by passing the stream through a carbon dioxide removal unit wherein it may be contacted with an aqueous solution of a base, for example sodium hydroxide (caustic solution wash). Hydrogen and methane may be separated from the other components by cryogenic distillation. Alternatively, hydrogen and methane may be separated together with the C2 hydrocarbons, comprising ethylene, any unconverted ethane and any acetylene, from any C3+ hydrocarbons in the product stream. The C2 hydrocarbons then need to be separated from the resulting stream comprising hydrogen, methane and C2 hydrocarbons. Acetylene may be removed by hydrogenating it into ethylene. Finally, ethane has to be separated from the ethylene, which may also be done by distillation. It is known to separate ethane from ethylene, by means of cryogenic distillation in so-called "C2 splitter" columns. In such cryogenic distillation, a relatively high pressure and a relatively low (cryogenic) temperature are applied to effect the separation of ethane from ethylene.

Further, it is known to oxidatively dehydrogenate ethane resulting in ethylene, in an oxidative dehydrogenation (oxydehydrogenation; ODH) process. Examples of ethane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. In said ethane ODH process oxygen ($O_2$) may be used as an oxidizing agent.

Still further, WO2018024650 discloses an integration of the two above-mentioned processes, namely steam cracking and ethane ODH. An object, according to said WO2018024650, for such integration is to establish a match between (i) the capacity of the steam cracker unit upstream of the downstream section in a steam cracker configuration and (ii) a higher capacity of the downstream section. In the invention of said WO2018024650, such match is established by feeding an effluent from an oxidative dehydrogenation (ODH) configuration to the steam cracker configuration, in which ODH configuration ethane is oxidatively dehydrogenated into ethylene and water, and wherein the effluent coming from the ODH configuration that is fed to the steam cracker configuration comprises unconverted ethane and ethylene. WO2018024650 discloses feeding the latter effluent to the steam cracker configuration at a position which is downstream of the steam cracker unit. Further, WO2018024650 discloses feeding unconverted ethane and ethylene from the stream comprising unconverted ethane and ethylene coming from a water condensation unit of the ODH configuration to a C2 separation unit of the steam cracker configuration.

However, as mentioned above, in an ethane ODH process oxygen ($O_2$) may be used as the oxidizing agent. Thus, in addition to ethylene and unconverted ethane, ethane ODH effluent may comprise unconverted oxygen. Generally, in order to avoid the risk of operating the ethane ODH process at oxygen depletion conditions, especially near the outlet of an ODH reactor, more oxygen is fed than required in which case the ethane ODH effluent comprises unconverted oxygen. However, on the other hand, having unconverted oxygen in the ODH effluent, at least a portion of which is fed to the steam cracker configuration in the ethane ODH/steam cracker integrated process of WO2018024650, increases the risk of explosion hazards because of the presence of hydrocarbons (including ethane and ethylene) in combination with a relatively high oxygen concentration in the back-end separation section (of the steam cracker configuration), in which section distillation may be applied to achieve the desired separations. In addition, such unconverted oxygen may be involved in some undesired trace chemistry, for example resulting in peroxides which as such could also result in an unwanted risk of explosion hazards.

Thus, a new safety and integrity risk caused by integration of steam cracking and ethane ODH is the introduction of small amounts of oxygen to the steam cracker process which is essentially oxygen-free. Small amounts of oxygen may leave the ethane ODH reactor due to incomplete oxygen conversion, even in the absence of process upsets. Additionally, process upsets likely result in significantly higher oxygen slippage from the ethane ODH reactor. This oxygen originating from the ethane ODH process poses safety and product specification risks: i) the oxygen is mixed with a hydrogen containing stream from the steam cracker leading to flammability risk; ii) higher oxygen concentrations in the back-end separation (distillation) section of the steam cracker configuration as mentioned above; and iii) undesired oxygenates may be formed in the product mixture.

In view of the above, it is an object of the present invention to remove unconverted oxygen originating from an ODH configuration before it can enter the back-end distillation section of a steam cracker configuration in an ethane ODH/steam cracker integrated process. Accordingly, it is an object of the present invention to provide a process for the production of ethylene, which comprises an ethane ODH/steam cracker integrated process, which process may be a technically advantageous, efficient and affordable process and in which process oxygen is removed upstream of the back-end distillation section of the steam cracker configuration. Such technically advantageous process would preferably also result in a lower energy demand and/or lower capital expenditure.

SUMMARY OF THE INVENTION

Surprisingly it was found that the above-mentioned object can be achieved by producing ethylene in an integrated configuration comprising (i) a steam cracker configuration which comprises a steam cracker unit, a water condensation unit and a carbon dioxide removal unit and (ii) an oxidative dehydrogenation (ODH) configuration which comprises an ODH unit and a water condensation unit wherein an effluent coming from the ODH configuration, which effluent comprises unconverted ethane and ethylene, is fed to the steam cracker configuration at a position which is downstream of the steam cracker unit, by removing unconverted oxygen, carbon monoxide and acetylene from at least a portion of the stream coming from the ODH unit by oxidation of carbon monoxide and acetylene into carbon dioxide in an oxidation unit which is located at a position (a) which is downstream of the ODH unit, and (b) which is downstream of the steam cracker unit and upstream of the carbon dioxide removal unit of the steam cracker configuration.

Accordingly, the present invention relates to a process for the production of ethylene in an integrated configuration comprising a steam cracker configuration and an oxidative dehydrogenation (ODH) configuration, wherein the steam cracker configuration comprises a steam cracker unit, a water condensation unit and a carbon dioxide removal unit and the ODH configuration comprises an ODH unit and a water condensation unit, which process comprises the following steps:
  subjecting a stream comprising saturated hydrocarbons to steam cracking conditions in the steam cracker unit, resulting in a stream comprising water, unconverted ethane, ethylene, acetylene, hydrogen, methane, carbon monoxide, carbon dioxide and C3+ hydrocarbons;
  feeding at least a portion of the stream coming from the steam cracker unit to the water condensation unit of the steam cracker configuration, and removing water and a portion of the C3+ hydrocarbons from said stream by condensation in the water condensation unit, resulting in a stream comprising unconverted ethane, ethylene, acetylene, hydrogen, methane, carbon monoxide, carbon dioxide and C3+ hydrocarbons;
  subjecting a stream comprising ethane and oxygen to oxidative dehydrogenation (ODH) conditions in the ODH unit, resulting in a stream comprising unconverted ethane, ethylene, acetylene, unconverted oxygen, water, carbon monoxide and carbon dioxide;
  feeding at least a portion of the stream coming from the ODH unit to the water condensation unit of the ODH configuration, and removing water from said stream by condensation in the water condensation unit, resulting in a stream comprising unconverted ethane, ethylene, acetylene, unconverted oxygen, carbon monoxide and carbon dioxide;
  feeding an effluent coming from the ODH configuration, which effluent comprises unconverted ethane and ethylene, to the steam cracker configuration at a position which is downstream of the steam cracker unit, preferably downstream of the water condensation unit of the steam cracker configuration;
  removing unconverted oxygen, carbon monoxide and acetylene from at least a portion of the stream coming from the ODH unit by oxidation of carbon monoxide and acetylene into carbon dioxide in an oxidation unit which is located at a position (a) which is downstream of the ODH unit, preferably downstream of the water condensation unit of the ODH configuration, and (b) which is downstream of the steam cracker unit, preferably downstream of the water condensation unit of the steam cracker configuration, and upstream of the carbon dioxide removal unit of the steam cracker configuration;
  feeding a stream comprising unconverted ethane, ethylene, optionally acetylene, hydrogen, methane, optionally carbon monoxide, carbon dioxide and C3+ hydrocarbons to the carbon dioxide removal unit of the steam cracker configuration, and removing carbon dioxide from said stream in the carbon dioxide removal unit of the steam cracker configuration, resulting in a stream comprising unconverted ethane, ethylene, optionally acetylene, hydrogen, methane, optionally carbon monoxide and C3+ hydrocarbons; and
  recovering unconverted ethane and ethylene from at least a portion of the stream coming from the carbon dioxide removal unit of the steam cracker configuration and optionally from at least a portion of the effluent coming from the ODH configuration, which effluent comprises unconverted ethane and ethylene, which is fed to the steam cracker configuration at a position which is downstream of the carbon dioxide removal unit of the steam cracker configuration.

BRIEF DESCRIPTION OF THE DRAWINGS

FIGS. 1 to 3 depict different embodiments of the present invention wherein an effluent coming from the ODH configuration, which effluent comprises unconverted ethane and ethylene, is fed to the steam cracker configuration at different positions.

DETAILED DESCRIPTION OF THE INVENTION

Figure 1:
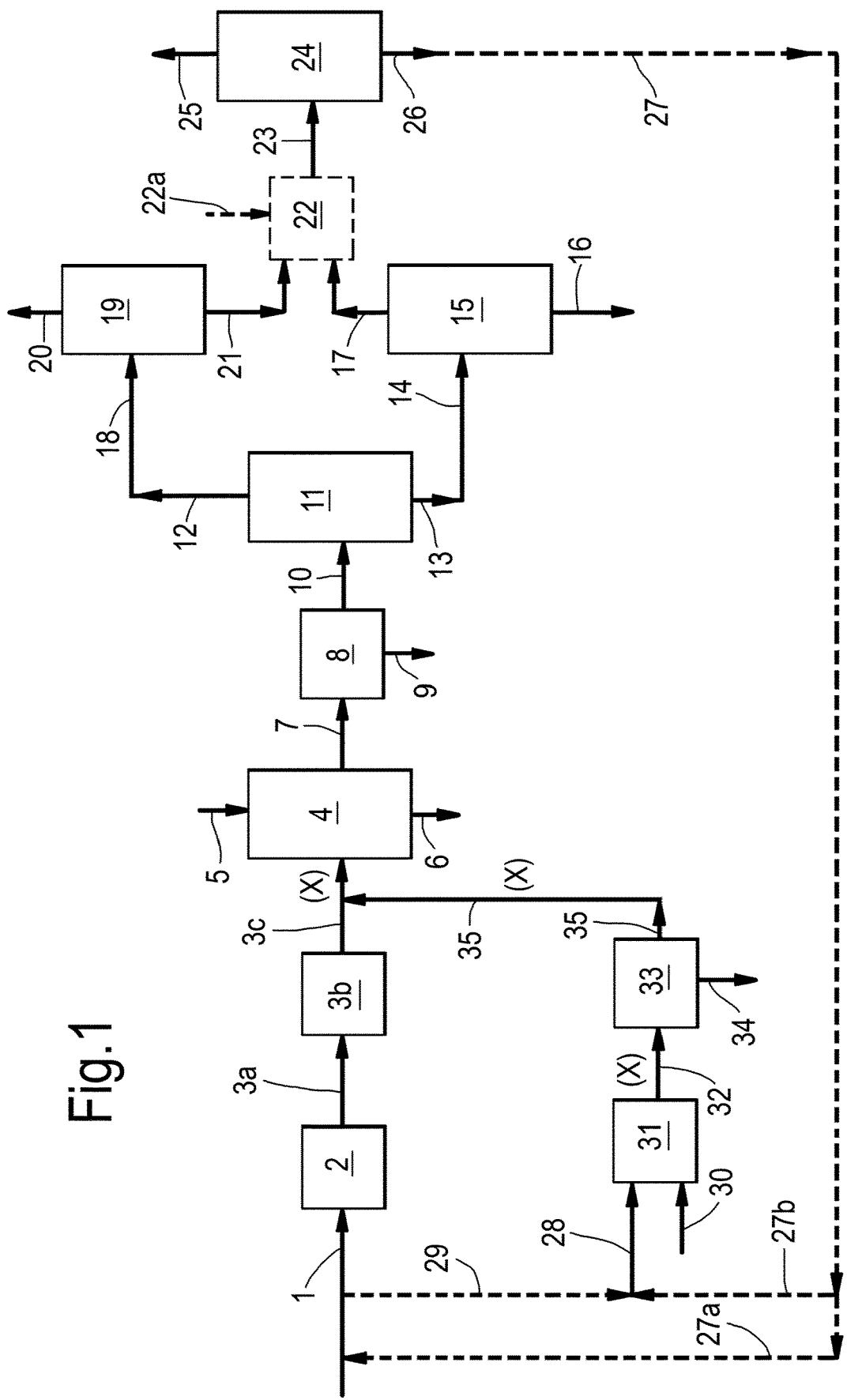

In the integrated process of the present invention, use is made of both a steam cracker configuration and an oxidative dehydrogenation (ODH) configuration.

The above-mentioned steam cracker configuration comprises:
  (a) a steam cracker unit wherein a stream comprising saturated hydrocarbons is subjected to steam cracking conditions, resulting in a stream comprising water, unconverted ethane, ethylene, acetylene, hydrogen, methane, carbon monoxide, carbon dioxide and C3+ hydrocarbons;
  (b) a water condensation unit to which at least a portion of the stream coming from the steam cracker unit is fed, and wherein water and a portion of the C3+ hydrocarbons is removed from said stream by condensation, resulting in a stream comprising unconverted ethane, ethylene, acetylene, hydrogen, methane, carbon monoxide, carbon dioxide and C3+ hydrocarbons;

(c) a carbon dioxide removal unit to which a stream comprising unconverted ethane, ethylene, optionally acetylene, hydrogen, methane, optionally carbon monoxide, carbon dioxide and C3+ hydrocarbons is fed, and wherein carbon dioxide is removed from said stream, resulting in a stream comprising unconverted ethane, ethylene, optionally acetylene, hydrogen, methane, optionally carbon monoxide and C3+ hydrocarbons.

Further, in the present invention, the steam cracker configuration may comprise a drying unit, a $1^{st}$ separation unit, a C2 separation unit, a $2^{nd}$ separation unit, as further described below, and optionally one or more separation units other than the above-mentioned separation units, an acetylene removal unit and/or one or more compressors (compression units).

The above-mentioned oxidative dehydrogenation (ODH) configuration comprises:

(i) an ODH unit wherein a stream comprising ethane and oxygen is subjected to oxidative dehydrogenation (ODH) conditions, resulting in a stream comprising unconverted ethane, ethylene, acetylene, unconverted oxygen, water, carbon monoxide and carbon dioxide;

(ii) a water condensation unit to which at least a portion of the stream coming from the ODH unit is fed, and wherein water is removed from said stream by condensation, resulting in a stream comprising unconverted ethane, ethylene, acetylene, unconverted oxygen, carbon monoxide and carbon dioxide.

Further, in the present invention, the ODH configuration may comprise a carbon dioxide removal unit and a drying unit.

In the present invention, the integration between the above-mentioned steam cracker configuration and ODH configuration is effected by feeding an effluent coming from the ODH configuration, which effluent comprises unconverted ethane and ethylene, to the steam cracker configuration at a position which is downstream of the steam cracker unit, preferably downstream of the water condensation unit of the steam cracker configuration.

Advantageously, in the present integrated process, the ODH unit enables full use of the entire capacity of the downstream section of a steam cracker configuration, in a situation wherein the capacity of a steam cracker unit upstream of said downstream section does not match the higher capacity of the downstream section. Thus, in the present invention, a relatively large amount of effluent, that is to say both effluent originating from the steam cracker unit and effluent originating from the ODH unit, can advantageously be fed to the downstream section of the steam cracker configuration.

Therefore, the present invention provides a process for the production of ethylene from saturated hydrocarbons, involving steam cracking of saturated hydrocarbons into ethylene and hydrogen, which process may be more technically advantageous, more efficient and more affordable. Such technically advantageous process may preferably result in a lower energy demand and/or lower capital expenditure.

In particular, by integrating an ODH configuration with a steam cracker configuration through feeding an effluent coming from the ODH configuration, which effluent comprises unconverted ethane and ethylene, to the steam cracker configuration, in particular to the downstream section of the steam cracker configuration, by feeding said effluent to the steam cracker configuration at a position which is downstream of the steam cracker unit, preferably downstream of the water condensation unit of the steam cracker configuration, the present invention is useful for debottlenecking an existing steam cracker configuration or expanding the total capacity of a steam cracker configuration. Advantageously, in this way, a relatively high capacity of the downstream section of a steam cracker configuration, as compared to the capacity of a steam cracker unit (comprising one or more furnaces) upstream of that downstream section, may be fully utilized. The foregoing may involve a case where a steam cracker furnace is close to or at the end of its lifetime. Further, this may involve a case where there is a desire to utilize the potential spare capacity in the back-end separation section of an existing steam cracker configuration because of additional design margin (overdesign of distillation towers or installation of higher capacity internals) and/or lower performance of the steam cracking furnace(s) than designed. The latter may also be a result of revamping an existing liquid steam cracker configuration to a gas (e.g. ethane) steam cracker configuration. Still further, this may apply to situations wherein 1 or more of a multitude of steam crackers has/have to be taken out of service (e.g. for maintenance or for any other reason). The foregoing examples show that the integration of the present invention may be advantageously applied in many practical situations, leading to a technically advantageous, efficient and affordable integrated process for the production of ethylene from saturated hydrocarbons, involving both steam cracking of saturated hydrocarbons into ethylene and hydrogen and oxidative dehydrogenation of ethane into ethylene and water.

In addition to enabling full utilization of the relatively high capacity of the downstream section of a steam cracker configuration as described above, the present invention also has the following additional advantages. An ethane ODH configuration, comprising an ODH unit (e.g. 1 ODH reactor) and a water condensation unit, involves a low footprint (less physical area needed), a low capital intensity, a low energy intensity and consequently a low overall $CO_2$ emissions intensity. In an ethane ODH process, less energy is needed in compressors and distillation towers, because the ODH off-gas is of higher molecular weight (ODH effluent has substantially no light components such as hydrogen and methane produced, as compared to for example steam cracking of saturated hydrocarbons), the ODH process may be operated at a high pressure (e.g. 2-10 bar) and finally it is an exothermic chemical process producing net high pressure steam, which steam can also advantageously be used in the integrated process of the present invention. In respect of the latter, steam produced in the ODH process may advantageously be used in the steam cracker configuration. And vice versa: any steam produced in the steam cracking process may advantageously be used in the ODH configuration. Further, generally, an ODH process produces much more concentrated product slate distribution (i.e. no or less by-products, like methane and C3+ hydrocarbons as produced in steam cracking), but yet ODH effluents are still chemically compatible with steam cracker effluents, making the line-up and separation requirement much simpler and less capital and energy intensive.

Further, in the integrated process of the present invention, an oxidation unit is used wherein unconverted oxygen, carbon monoxide and acetylene are removed from at least a portion of the stream coming from the ODH unit by oxidation of carbon monoxide and acetylene into carbon dioxide, which oxidation unit is located at a position (a) which is downstream of the ODH unit, and (b) which is downstream of the steam cracker unit and upstream of the carbon dioxide removal unit of the steam cracker configuration. In this oxidation step, unconverted oxygen originating from the ODH unit functions as an oxidizing agent, oxidizing carbon monoxide and acetylene into carbon dioxide. One of the advantages associated with having such oxidation unit in the present invention, is that the ethane ODH process in the ODH unit can be more robust, implying that (i) more oxygen may be fed to the ODH unit than needed and (ii) no deep oxygen conversion is required in the ODH unit, thereby enabling higher ethane conversions in that unit.

Further, the above-described location of the oxidation unit in the present integrated process advantageously results in that unconverted oxygen originating from the ODH configuration is removed before it can enter the back-end distillation section of the steam cracker configuration, thereby avoiding the safety and integrity risks, associated with the presence of oxygen in such back-end section, as discussed in the introduction of the present specification. Additionally, by positioning the oxidation unit upstream of the carbon dioxide removal unit of the steam cracker configuration, additional carbon dioxide generated in the oxidation unit by oxidation of carbon monoxide and acetylene, using the unconverted oxygen, can be removed in said carbon dioxide removal unit together with the carbon dioxide produced in the steam cracker unit. Still further, by positioning the oxidation unit upstream of the carbon dioxide removal unit of the steam cracker configuration, carbon dioxide may advantageously still function as a diluent before it is removed, in particular as a heat sink in the oxidation unit wherein heat is released due to the oxidation of carbon monoxide and acetylene.

These and more advantages of the present invention will also be apparent from the following detailed description.

Within the present specification, the following terms have the following meanings.

"C3+ hydrocarbons" comprise hydrocarbons having a carbon number of 3 or higher. C3+ hydrocarbons may comprise propane and/or propylene.

"C2+ hydrocarbons" comprise hydrocarbons having a carbon number of 2 or higher. C2+ hydrocarbons may comprise ethane, ethylene, acetylene, propane and/or propylene.

"C2 hydrocarbons" comprise hydrocarbons having a carbon number of 2. C2 hydrocarbons may comprise ethane, ethylene and/or acetylene.

In respect of the process of the present invention, "steam cracker unit" means a unit wherein saturated hydrocarbons are converted, by subjecting them to steam cracking conditions, into ethylene and hydrogen. The steam cracker unit may comprise a furnace.

In respect of the process of the present invention, "oxidative dehydrogenation unit" means a unit wherein ethane is converted, by subjecting it to oxidative dehydrogenation (ODH) conditions, into ethylene and water. The ODH unit may comprise a reactor, which may be a catalytic reactor which is a reactor that contains a catalyst.

In respect of the process of the present invention, "carbon dioxide removal unit" means a unit wherein carbon dioxide is removed from a stream comprising ethylene and carbon dioxide. Carbon dioxide removal agent as fed to the carbon dioxide removal unit may be an aqueous solution of a base, for example sodium hydroxide or an amine.

In respect of the process of the present invention, "drying unit" means a unit wherein water is removed from a stream comprising ethylene and water.

In respect of the process of the present invention, "acetylene removal unit" means a unit wherein acetylene is removed from a stream comprising acetylene, ethylene and optionally unconverted ethane, which removal may be carried out by converting the acetylene, by subjecting it to hydrogenation conditions, into ethylene. In case the acetylene removal unit is an acetylene hydrogenation unit, it may comprise a reactor, which may be a catalytic reactor which is a reactor that contains a catalyst.

In respect of the process of the present invention, "C2 separation unit" means a unit wherein ethylene is separated from ethane. Ethylene may be separated from ethane in any way, for example by means of distillation, absorption, adsorption or a membrane.

Further, while the process and configurations of the present invention and the stream or streams used in said process are described in terms of "comprising", "containing" or "including" one or more various described steps or units or components, they can also "consist essentially of" or "consist of" said one or more various described steps or units or components.

In the context of the present invention, in a case where a stream comprises two or more components, these components are to be selected in an overall amount not to exceed 100 vol. % or 100 wt. %.

As described above, in the present invention, the integration between the above-mentioned steam cracker configuration and ODH configuration is effected by feeding an effluent coming from the ODH configuration, which effluent comprises unconverted ethane and ethylene, to the steam cracker configuration at a position which is downstream of the steam cracker unit, preferably downstream of the water condensation unit of the steam cracker configuration. Further, suitably, no unconverted ethane from an effluent coming from the steam cracker configuration is fed to the ODH unit of the ODH configuration, with the exception of an optional recycle of unconverted ethane from an effluent coming from a C2 separation unit of the steam cracker configuration to the ODH unit of the ODH configuration. Still further, suitably, ethane is fed to the ODH unit which originates from one or more sources selected from the group consisting of a) a source of fresh ethane that is used to feed ethane to the steam cracker unit; b) another source of fresh ethane, other than said first source mentioned under a); and c) unconverted ethane as recovered in the present process.

Generally, in the present invention, the feed to the ODH unit may comprise: 1) unconverted ethane and no fresh ethane; or 2) unconverted ethane and fresh ethane; or 3) fresh ethane and no unconverted ethane. Likewise, generally, in the present invention, the feed to the steam cracker unit may comprise: 1) unconverted ethane and no fresh ethane; or 2) unconverted ethane and fresh ethane; or 3) fresh ethane and no unconverted ethane. In particular, fresh ethane may be fed to the ODH unit. Further, in particular, fresh ethane may be fed to the steam cracker unit. Still further, in particular, fresh ethane may be fed both to the ODH unit and to the steam cracker unit. As described above, feeding fresh ethane implies feeding ethane that was not subjected to steam cracking conditions and neither to oxidative dehydrogenation (ODH) conditions. Fresh ethane as fed to the ODH unit and fresh ethane as fed to the steam cracker unit may originate from the same source or different sources.

Further, in the present invention, saturated hydrocarbons are fed to the steam cracker unit which comprise one or more of ethane, propane, butane, liquefied petroleum gas (LPG), naphtha, hydrowax and recycled waste plastics oil, preferably ethane and/or naphtha, more preferably ethane.

In the present process, the effluent coming from the ODH configuration, which effluent comprises unconverted ethane and ethylene and which effluent is fed to the steam cracker configuration, may be the stream comprising unconverted ethane and ethylene coming from the water condensation unit of the ODH configuration. Preferably, unconverted ethane and ethylene from the stream comprising unconverted ethane and ethylene coming from the water condensation unit of the ODH configuration are fed to a C2 separation unit of the steam cracker configuration.

Further, as described above, in the present invention, unconverted oxygen, carbon monoxide and acetylene are removed from at least a portion of the stream coming from the ODH unit by oxidation of carbon monoxide and acetylene into carbon dioxide in an oxidation unit which is located at a position (a) which is downstream of the ODH unit, preferably downstream of the water condensation unit of the ODH configuration, and (b) which is downstream of the steam cracker unit, preferably downstream of the water condensation unit of the steam cracker configuration, and upstream of the carbon dioxide removal unit of the steam cracker configuration.

In one embodiment of the present invention, hereinafter also referred to as "Embodiment A", it is preferred that the oxidation unit is part of the steam cracker configuration and is located at a position (a) which is downstream of the position at which the effluent coming from the ODH configuration, which effluent comprises unconverted ethane and ethylene, is fed to the steam cracker configuration, wherein said effluent additionally comprises acetylene, unconverted oxygen, carbon monoxide and optionally carbon dioxide, and (b) which is upstream of the carbon dioxide removal unit of the steam cracker configuration.

Figure 2:
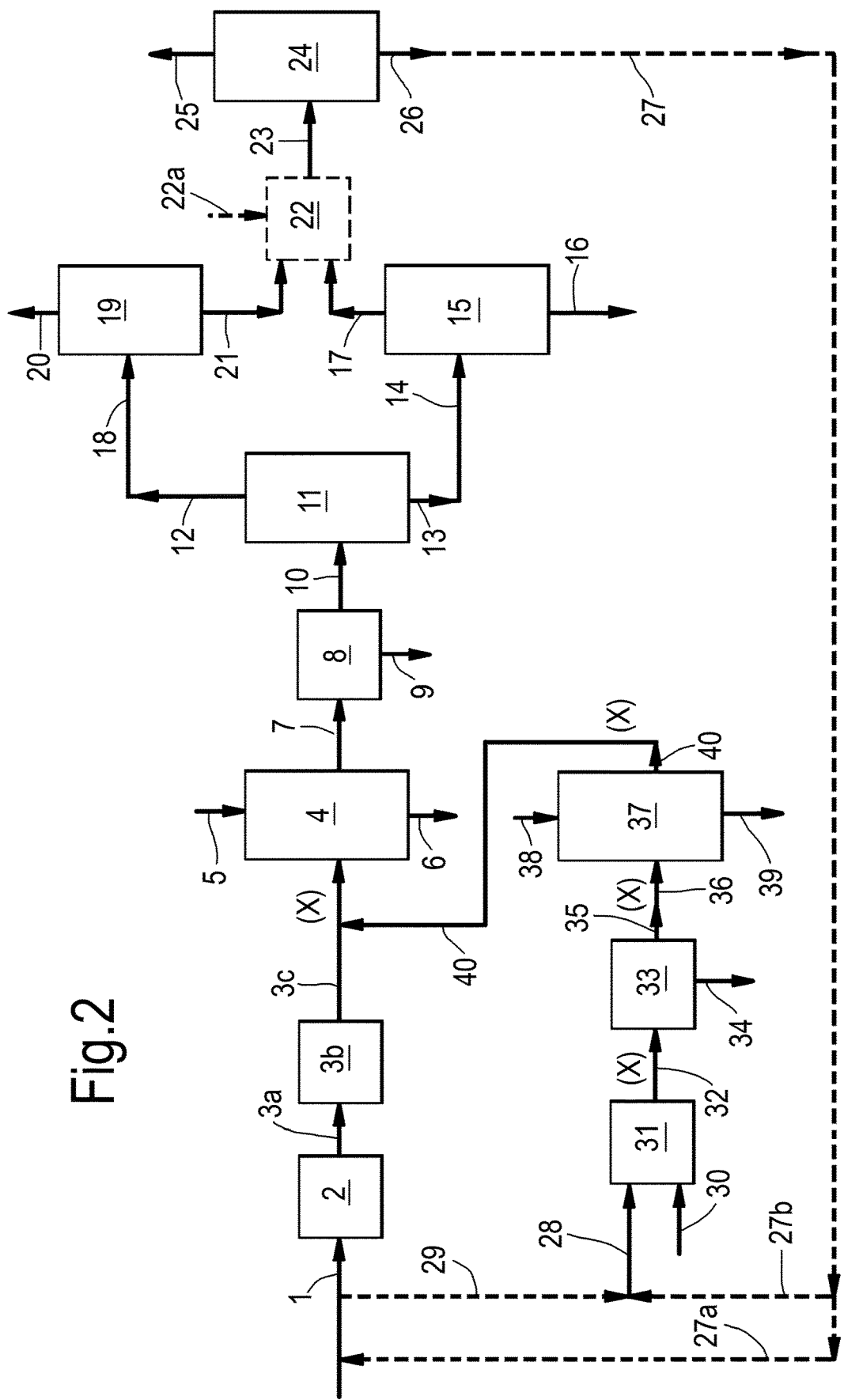

Embodiment A of the present process may be practiced in the processes as depicted in FIGS. 1 and 2 as further described below. In Embodiment A, both (i) unconverted oxygen, carbon monoxide and acetylene from at least a portion of the stream coming from the ODH unit and (ii) carbon monoxide and acetylene from at least a portion of the stream coming from the steam cracker unit are removed in the oxidation unit by oxidation of carbon monoxide and acetylene into carbon dioxide. In Embodiment A, the steam cracker configuration may or may not comprise an acetylene removal unit at a position which is downstream of the carbon dioxide removal unit of the steam cracker configuration. It is preferred that in Embodiment A, the steam cracker configuration does not comprise an acetylene removal unit, especially in a case wherein all or substantially all of the acetylene originating from the steam cracker and ODH units is removed in the oxidation unit. Such steam cracker configuration without an acetylene removal unit may be preferred in a so-called "greenfield application", wherein an ODH configuration is to be integrated with a not yet existing steam cracker configuration, because not having to include and not having to use such acetylene removal unit may result in a lower energy demand and/or lower capital expenditure.

In another embodiment of the present invention, hereinafter also referred to as "Embodiment B", it is preferred that the oxidation unit is part of the ODH configuration and is located at a position (a) which is upstream or downstream, preferably downstream, of the water condensation unit of the ODH configuration, and (b) which is upstream or downstream, preferably upstream, of an optional carbon dioxide removal unit of the ODH configuration, and (c) which is upstream of the position at which the effluent coming from the ODH configuration, which effluent comprises unconverted ethane and ethylene, is fed to the steam cracker configuration, wherein said effluent additionally comprises optionally carbon dioxide.

Embodiment B of the present process may be practiced in the processes as depicted in FIGS. 1, 2 and 3 as further described below. In Embodiment B, unconverted oxygen, carbon monoxide and acetylene from at least a portion of the stream coming from the ODH unit, but not carbon monoxide and acetylene originating from the steam cracker unit, are removed in the oxidation unit by oxidation of carbon monoxide and acetylene into carbon dioxide. In Embodiment B, it is preferred that the steam cracker configuration comprises an acetylene removal unit at a position which is downstream of the carbon dioxide removal unit of the steam cracker configuration, because acetylene originating from the steam cracker unit is not removed in the oxidation unit. Such steam cracker configuration with an acetylene removal unit may be preferred in a so-called "brownfield application", wherein an ODH configuration is to be integrated with an existing steam cracker configuration which already comprises such acetylene removal unit. However, also for the "greenfield application" mentioned above with respect to Embodiment A, wherein an ODH configuration is to be integrated with a not yet existing steam cracker configuration, it may still be preferred in Embodiment B that the steam cracker configuration comprises an acetylene removal unit, for example so as to convert acetylene originating from the steam cracker unit into the desired ethylene by means of hydrogenation, instead of oxidizing it to carbon dioxide which oxidation would occur in above-described Embodiment A. Furthermore, in case such acetylene hydrogenation unit is used as acetylene removal unit, acetylene may be selectively hydrogenated to ethylene, thereby advantageously resulting in that no or substantially no ethylene is hydrogenated to ethane. Any known acetylene hydrogenation catalyst may be used.

In the present process, the steam cracker configuration may additionally comprise a $1^{st}$ separation unit, and the effluent coming from the ODH configuration, which effluent comprises unconverted ethane and ethylene, may be fed to the steam cracker configuration at a position which is upstream of the $1^{st}$ separation unit, and the process may additionally comprise the following steps:

feeding at least a portion of the stream coming from the carbon dioxide removal unit of the steam cracker configuration and optionally at least a portion of the effluent coming from the ODH configuration, which effluent comprises unconverted ethane and ethylene, which is fed to the steam cracker configuration at a position which is downstream of the carbon dioxide removal unit of the steam cracker configuration, to the $1^{st}$ separation unit; and separating said stream or streams in the $1^{st}$ separation unit into a stream comprising hydrogen, methane and optionally carbon monoxide and a stream comprising C3+ hydrocarbons.

In the present process, in case the steam cracker configuration additionally comprises the above-mentioned $1^{st}$ separation unit, and the effluent coming from the ODH configuration, which effluent comprises unconverted ethane and ethylene, is fed to the steam cracker configuration at a position which is upstream of the $1^{st}$ separation unit, and the process comprises the above-mentioned additional steps, the steam cracker configuration may additionally comprise a C2 separation unit, and the process may additionally comprises the following steps:

feeding unconverted ethane and ethylene from a stream comprising unconverted ethane, ethylene, optionally acetylene, hydrogen, methane, optionally carbon monoxide and C3+ hydrocarbons to the C2 separation unit; and separating said stream in the C2 separation unit into a stream comprising ethylene and a stream comprising unconverted ethane;

wherein:

unconverted ethane and ethylene from the stream comprising unconverted ethane and ethylene coming from the water condensation unit of the ODH configuration are fed to the C2 separation unit.

Optionally, in the present invention, unconverted ethane from the stream comprising unconverted ethane coming from the C2 separation unit may be recycled to the steam cracker unit and/or the ODH unit.

In the present process, in case the steam cracker configuration additionally comprises the above-mentioned $1^{st}$ separation unit and C2 separation unit, and the effluent coming from the ODH configuration, which effluent comprises unconverted ethane and ethylene, is fed to the steam cracker configuration at a position which is upstream of the $1^{st}$ separation unit, and the process comprises the above-mentioned additional steps, the steam cracker configuration may additionally comprise a $2^{nd}$ separation unit, and the process may additionally comprise the following steps:

1) in a first embodiment:

separating a stream comprising unconverted ethane, ethylene, optionally acetylene, hydrogen, methane, optionally carbon monoxide and C3+ hydrocarbons in the $1^{st}$ separation unit into a stream comprising hydrogen, methane and optionally carbon monoxide and a stream comprising C2+ hydrocarbons, which C2+ hydrocarbons comprise unconverted ethane, ethylene, optionally acetylene and C3+ hydrocarbons;

feeding at least a portion of the separated stream comprising C2+ hydrocarbons coming from the $1^{st}$ separation unit to the $2^{nd}$ separation unit wherein said stream is separated into a stream comprising C2 hydrocarbons, which C2 hydrocarbons comprise unconverted ethane, ethylene and optionally acetylene, and a stream comprising C3+ hydrocarbons; and feeding unconverted ethane and ethylene from the separated stream comprising C2 hydrocarbons coming from the $2^{nd}$ separation unit to the C2 separation unit wherein they are separated into a stream comprising ethylene and a stream comprising unconverted ethane; or 2) in a second embodiment:

separating a stream comprising unconverted ethane, ethylene, optionally acetylene, hydrogen, methane, optionally carbon monoxide and C3+ hydrocarbons in the $1^{st}$ separation unit into a stream comprising hydrogen, methane, optionally carbon monoxide and C2 hydrocarbons, which C2 hydrocarbons comprise unconverted ethane, ethylene and optionally acetylene, and a stream comprising C3+ hydrocarbons;

feeding at least a portion of the separated stream comprising hydrogen, methane, optionally carbon monoxide and C2 hydrocarbons coming from the $1^{st}$ separation unit to a $2^{nd}$ separation unit wherein said stream is separated into a stream comprising hydrogen, methane and optionally carbon monoxide and a stream comprising C2 hydrocarbons; and feeding unconverted ethane and ethylene from the separated stream comprising C2 hydrocarbons coming from the $2^{nd}$ separation unit to the C2 separation unit wherein they are separated into a stream comprising ethylene and a stream comprising unconverted ethane.

In alternative embodiments other than the above-described first and second embodiments, the separations in the back-end separation section of the steam cracker configuration may be carried out in different ways. In the following two alternative embodiments methane is removed in a final step of the separation schemes, whereas in the above-described first embodiment such methane removal takes place in a first step (in the $1^{st}$ separation unit) and in the above-described second embodiment such methane removal takes place in a second step (in the $2^{nd}$ separation unit).

In a first alternative embodiment, the separation scheme comprises the following separation steps, wherein the presence of any hydrogen, acetylene and/or carbon monoxide is not mentioned:

i) separating a stream comprising unconverted ethane, ethylene, methane and C3+ hydrocarbons into a stream comprising methane and C2 hydrocarbons, which C2 hydrocarbons comprise unconverted ethane and ethylene, and a stream comprising C3+ hydrocarbons, which step i) may be carried out in the above-described $1^{st}$ separation unit;

ii) separating at least a portion of the stream comprising methane and C2 hydrocarbons resulting from step i) into a stream comprising methane and ethylene and a stream comprising unconverted ethane, which step ii) may be carried out in the above-described C2 separation unit; and iii) separating at least a portion of the stream comprising methane and ethylene resulting from step ii) into a stream comprising methane and a stream comprising ethylene.

In a second alternative embodiment, the separation scheme comprises the following separation steps, wherein the presence of any hydrogen, acetylene and/or carbon monoxide is not mentioned:

i) separating a stream comprising unconverted ethane, ethylene, methane and C3+ hydrocarbons into a stream comprising methane and ethylene and a stream comprising unconverted ethane and C3+ hydrocarbons, which step i) may be carried out in the above-described $1^{st}$ separation unit or C2 separation unit;

ii) separating at least a portion of the stream comprising unconverted ethane and C3+ hydrocarbons resulting from step i) into a stream comprising unconverted ethane and a stream comprising C3+ hydrocarbons; and iii) separating at least a portion of the stream comprising methane and ethylene resulting from step i) into a stream comprising methane and a stream comprising ethylene.

In the above-described separations and separation units, the separation may be carried out in any way, for example by means of distillation, absorption, adsorption and/or a membrane.

Further, in the present process, the stream coming from the carbon dioxide removal unit of the steam cracker configuration may comprise acetylene, and the steam cracker configuration may additionally comprise an acetylene removal unit, and the process may additionally comprise the following step:

an acetylene removal step wherein in the acetylene removal unit acetylene is removed from a stream comprising acetylene, ethylene and optionally unconverted ethane.

In the above-mentioned acetylene removal step, acetylene may be removed in any way, for example by means of absorption of acetylene or by means of conversion (i.e. hydrogenation) of acetylene into ethylene. An example of a selective acetylene absorption agent is dimethyl formamide (DMF). Preferably, in the above-mentioned acetylene removal step, in an acetylene hydrogenation unit as the acetylene removal unit a stream comprising acetylene, ethylene and optionally unconverted ethane is subjected to hydrogenation conditions so as to convert acetylene into ethylene.

In case in the present process, the steam cracker configuration additionally comprises the above-mentioned acetylene removal unit and the process additionally comprises the above-mentioned acetylene removal step, said acetylene removal unit may be located at any position which is downstream of the carbon dioxide removal unit of the steam cracker configuration, including: i) a position which is upstream of the $1^{st}$ separation unit; ii) a position which is between the $1^{st}$ separation unit and the $2^{nd}$ separation unit; and iii) a position which is between the $2^{nd}$ separation unit and the C2 separation unit. Said option iii) is illustrated in FIGS. 1-3 (by acetylene hydrogenation unit 22). Further, said option ii) may be preferred in the above-mentioned second embodiment wherein a stream resulting from the $1^{st}$ separation unit is a stream comprising hydrogen, methane, optionally carbon monoxide and C2 hydrocarbons, which C2 hydrocarbons comprise unconverted ethane, ethylene and acetylene, which hydrogen may advantageously be used as a hydrogenating agent to hydrogenate the acetylene as contained in that same stream, so that less or no additional hydrogenating agent needs to be added to the acetylene removal step in case said step is an acetylene hydrogenation step. Still further, preferably, said acetylene removal unit is not located at a position which is downstream of the C2 separation unit and upstream of any recycle of unconverted ethane. In case the present process comprises an acetylene hydrogenation step as an acetylene removal step, a stream containing hydrogen may be fed to the acetylene removal unit of the steam cracker configuration. Hydrogen is a hydrogenation agent which may hydrogenate acetylene into ethylene and which may be derived from the steam cracker configuration.

In the present invention, in the carbon dioxide removal unit of the steam cracker configuration, carbon dioxide is removed from a stream comprising unconverted ethane, ethylene, optionally acetylene, hydrogen, methane, optionally carbon monoxide, carbon dioxide and C3+ hydrocarbons. In above-mentioned Embodiment B, wherein the oxidation unit is part of the ODH configuration, the latter stream comprises acetylene and carbon monoxide. In above-mentioned Embodiment A, wherein the oxidation unit is part of the steam cracker configuration, the latter stream may or may not comprise acetylene and carbon monoxide. Further, in the present invention, the latter stream may comprise at least a portion of the stream coming from the water condensation unit of the steam cracker configuration (as illustrated in FIG. 3 by line 3c), and optionally at least a portion of the effluent coming from the ODH configuration, which effluent comprises unconverted ethane and ethylene, which is fed to the steam cracker configuration at a position which is downstream of the water condensation unit of the steam cracker configuration (as illustrated in FIG. 1 by lines 3c and line 35, respectively, and in FIG. 2 by lines 3c and line 40, respectively). Optionally, in case the stream comprising unconverted ethane, ethylene, optionally acetylene, hydrogen, methane, optionally carbon monoxide and C3+ hydrocarbons, resulting from the carbon dioxide removal step, comprises water, the stream is fed to a drying unit as part of the steam cracker configuration in order to remove the water. Preferably, said water is removed in said drying unit located at a position which is upstream of the above-mentioned $1^{st}$ separation unit.

Still further, in the above-described process, the stream comprising unconverted ethane, ethylene, acetylene, unconverted oxygen, carbon monoxide and carbon dioxide coming from the water condensation unit of the ODH configuration may be fed to a carbon dioxide removal unit which is part of the ODH configuration, wherein carbon dioxide is removed from said stream resulting in a stream comprising unconverted ethane, ethylene, acetylene, unconverted oxygen and carbon monoxide. Optionally, in case the stream comprising unconverted ethane, ethylene, acetylene, unconverted oxygen and carbon monoxide, resulting from the carbon dioxide removal step, comprises water, the stream may be fed to a drying unit as part of the ODH configuration in order to remove the water.

Still further, in the above-described process, an effluent coming from the ODH configuration, which effluent comprises unconverted ethane and ethylene, is fed to the steam cracker configuration. Suitably, said effluent coming from the ODH configuration is an effluent originating, either directly or indirectly, from the water condensation unit of the ODH configuration. Thus, advantageously, in the present invention, the water condensation units of the ODH and steam cracker configurations are not integrated into one water condensation unit, due the possible presence of acetic acid in effluent coming from the ODH unit.

In the above-described process, the above-mentioned effluent coming from the ODH configuration which effluent is fed to the steam cracker configuration, may be the stream coming from the water condensation unit of the ODH configuration. Preferably, the stream coming from the water condensation unit of the ODH configuration is fed to to the steam cracker configuration at a position which is downstream of the water condensation unit of the steam cracker configuration and upstream of the carbon dioxide removal unit of the steam cracker configuration. This is illustrated in FIG. 1 (by line 35).

Further, in the above-described process, the above-mentioned effluent coming from the ODH configuration which effluent is fed to the steam cracker configuration, may be the stream coming from the optional carbon dioxide removal unit of the ODH configuration. Preferably, the stream coming from the optional carbon dioxide removal unit of the ODH configuration is fed to the steam cracker configuration at a position which is downstream of the water condensation unit of the steam cracker configuration and upstream of the carbon dioxide removal unit of the steam cracker configuration. This is illustrated in FIG. 2 (by line 40).

Further, in a case wherein the streams resulting from the carbon dioxide removal steps comprise water and the ODH configuration comprises a drying unit, as described above, the stream coming from the drying unit of the ODH configuration may be fed to the above-mentioned $1^{st}$ separation unit of the steam cracker configuration, in which $1^{st}$ separation unit a stream comprising unconverted ethane, ethylene, optionally acetylene, hydrogen, methane, optionally carbon monoxide and C3+ hydrocarbons is separated into a stream comprising hydrogen, methane and optionally carbon monoxide and a stream comprising C2+ hydrocarbons (above-described "first embodiment"). This is illustrated in FIG. 3 (by line 45). Further, in a case wherein the streams resulting from the carbon dioxide removal steps comprise water and the ODH configuration comprises a drying unit, as described above, the stream coming from the drying unit of the ODH configuration may be fed to the 2$^{nd}$ separation unit of the steam cracker configuration, in which 2$^{nd}$ separation unit at least a portion of a separated stream comprising hydrogen, methane, optionally carbon monoxide and C2 hydrocarbons coming from the 1$^{st}$ separation unit is separated into a stream comprising hydrogen, methane and optionally carbon monoxide and a stream comprising C2 hydrocarbons (above-described "second embodiment"). This is also illustrated in FIG. 3 (by line 46).

In the process of the present invention, a stream comprising saturated hydrocarbons is subjected to steam cracking conditions in a steam cracker unit which is part of a steam cracker configuration, resulting in a stream comprising water, unconverted ethane, ethylene, acetylene, hydrogen, methane, carbon monoxide, carbon dioxide and C3+ hydrocarbons. Suitable steam cracking conditions for this steam cracking step are described hereinbelow.

Suitably, in the above-mentioned steam cracking step, no oxygen containing stream is fed to the steam cracker unit since there is no need to use oxygen as an oxidizing agent. However, carbon dioxide may still be produced as an impurity in the presence of oxygen (resulting from some small air ingress into the steam cracker unit) and/or in water-shift reactions of hydrocarbons. Further, carbon monoxide and carbon dioxide may enter the steam cracking process as contaminants in the feed.

Further, suitably, in the above-mentioned steam cracking step, no catalyst is used. Preferably, said steam cracking step is performed at an elevated temperature, more preferably in the range of from 650 to 1000° C., most preferably of from 750 to 950° C. Hydrocarbon steam cracking processes are well known. Reference is for instance made to Kniel et al., Ethylene, Keystone to the petrochemical industry, Marcel Dekker, Inc, New York, 1980, in particular chapter 6 and 7. The above-mentioned steam cracking conditions involve the addition of steam (water vapor) to said steam cracking step which steam ends up in the stream coming from said steam cracker unit, which water is removed in the water condensation unit of the steam cracker configuration.

In the process of the present invention, a stream comprising ethane and oxygen is subjected to oxidative dehydrogenation (ODH) conditions in an ODH unit which is part of an ODH configuration, resulting in a stream comprising unconverted ethane, ethylene, acetylene, unconverted oxygen, water, carbon monoxide and carbon dioxide. Suitable ODH conditions for this ODH step are described hereinbelow.

In the above-mentioned ODH step, ethane is contacted with oxygen (O$_2$). Said oxygen is the oxidizing agent in the ODH reaction. In the ODH step, oxygen (O$_2$) and ethane are fed to the ODH unit. The ODH unit may comprise a reactor, which reactor may contain an ODH catalyst, in particular a mixed metal oxide catalyst containing molybdenum, vanadium, optionally niobium and optionally tellurium. Oxygen and ethane are then contacted with said catalyst in the ODH reactor, resulting in oxidative dehydrogenation of the ethane.

In the ODH step of the process of the present invention, oxygen and ethane may be fed to the reactor together or separately. That is to say, one or more feed streams, suitably gas streams, comprising one or more of said 2 components may be fed to the reactor. For example, one feed stream comprising oxygen and ethane may be fed to the reactor. Alternatively, two or more feed streams, suitably gas streams, may be fed to the reactor, which feed streams may form a combined stream inside the reactor. For example, one feed stream comprising oxygen and another feed stream comprising ethane may be fed to the reactor separately.

Further, in the ODH step of the process of the present invention, suitably during contacting oxygen and ethane with an ODH catalyst, the temperature is of from 300 to 500° C. More preferably, said temperature is of from 310 to 450° C., more preferably of from 320 to 420° C., most preferably of from 330 to 420° C.

Still further, in the above-mentioned ODH step, suitably during contacting the oxygen and ethane with an ODH catalyst, typical pressures are 0.1-30 or 0.1-20 bara (i.e. "bar absolute"). Further, preferably, said pressure is of from 0.1 to 15 bara, more preferably of from 1 to 8 bara, most preferably of from 3 to 8 bara.

The product of the above-mentioned ODH step comprises the dehydrogenated equivalent of ethane, that is to say ethylene. Ethylene is initially formed in said step. However, in said same step, ethylene may be further oxidized under the same conditions into the corresponding carboxylic acid, that is to say acetic acid.

In addition to oxygen and ethane, an inert gas may also be fed to the ODH reactor. Said inert gas may be selected from the group consisting of the noble gases and nitrogen (N$_2$). Preferably, the inert gas is nitrogen or argon, more preferably nitrogen. Said oxygen is an oxidizing agent, thereby resulting in oxidative dehydrogenation of ethane. Said oxygen may originate from any source, such as for example air. Ranges for the molar ratio of oxygen to ethane which are suitable, are of from 0.01 to 1, more suitably 0.05 to 0.5. Said ratio of oxygen to ethane is the ratio before oxygen and ethane are contacted with the catalyst. In other words, said ratio of oxygen to ethane is the ratio of oxygen as fed to ethane as fed. Obviously, after contact with the catalyst, at least part of the oxygen and ethane gets consumed.

Preferably, in the ODH step of the process of the present invention, the ODH catalyst is a heterogeneous catalyst. Further, preferably, the ODH catalyst is a mixed metal oxide catalyst containing molybdenum, vanadium, optionally niobium and optionally tellurium as the metals, which catalyst may have the following formula:

wherein:
- a, b, c and n represent the ratio of the molar amount of the element in question to the molar amount of molybdenum (Mo);
- a (for V) is from 0.01 to 1, preferably 0.05 to 0.60, more preferably 0.10 to 0.40, more preferably 0.20 to 0.35, most preferably 0.25 to 0.30;
- b (for Te) is 0 or from >0 to 1, preferably 0.01 to 0.40, more preferably 0.05 to 0.30, more preferably 0.05 to 0.20, most preferably 0.09 to 0.15;
- c (for Nb) is 0 or from >0 to 1, preferably 0.01 to 0.40, more preferably 0.05 to 0.30, more preferably 0.10 to 0.25, most preferably 0.14 to 0.20; and
- n (for O) is a number which is determined by the valency and frequency of elements other than oxygen.

The amount of the catalyst in the above-mentioned ODH step is not essential. Preferably, a catalytically effective amount of the catalyst is used, that is to say an amount sufficient to promote the ethane oxydehydrogenation reaction.

The ODH reactor that may be used in the above-mentioned ODH step may be any reactor, including fixed-bed and fluidized-bed reactors. Suitably, the reactor is a fixed-bed reactor.

Examples of oxydehydrogenation processes, including catalysts and process conditions, are for example disclosed in above-mentioned U.S. Pat. No. 7,091,377, WO2003064035, US20040147393, WO2010096909 and US20100256432, the disclosures of which are herein incorporated by reference.

Water is formed during the ethane ODH reaction that takes place in the ODH step of the present process, and is removed in the water condensation unit of the ODH configuration.

In the present invention, water may be removed from streams containing water in the water condensation units of the steam cracker and ODH configurations by any one of well-known methods. In these water condensation steps, water may easily be condensed by cooling down the stream in question to a lower temperature, for example room temperature, after which the condensed water in combination with any acetic acid (in the ODH configuration) or a portion of the C3+ hydrocarbons (in the steam cracker configuration) can be separated from the remaining (gaseous) stream. Further, additional water may be fed to said water condensation units, for example to the water condensation unit of the ODH configuration. Advantageously, in the present invention, the water condensation units of the ODH and steam cracker configurations are not integrated into one water condensation unit, due the possible presence of acetic acid in effluent coming from the ODH unit.

In the present invention, carbon dioxide may be removed from streams containing carbon dioxide in the carbon dioxide removal unit of the steam cracker configuration and the optional carbon dioxide removal unit of the ODH configuration by any one of well-known methods. As mentioned above, a suitable carbon dioxide removal agent that may be fed to a carbon dioxide removal unit may be an aqueous solution of a base, for example sodium hydroxide or an amine. After such carbon dioxide removal, the stream should be dried in a drying unit to remove residual water from the stream. Contacting an aqueous solution of an amine with a carbon dioxide containing stream is preferred in a case where the carbon dioxide amount is relatively high, for example in the case of an ethane ODH effluent. Contacting an aqueous solution of sodium hydroxide with a carbon dioxide containing stream is preferred in a case where the carbon dioxide amount is relatively low, for example 1) in the case of a steam cracker effluent, especially an ethane steam cracker effluent, or 2) in the case of an ethane ODH effluent that was treated with an aqueous solution of an amine and which still contains some residual carbon dioxide. In the present invention, the carbon dioxide removal unit of the steam cracker configuration and/or the optional carbon dioxide removal unit of the ODH configuration may comprise a subunit wherein carbon dioxide is removed by an aqueous solution of an amine and a downstream subunit wherein carbon dioxide is removed by an aqueous solution of sodium hydroxide. It may be preferred that carbon dioxide containing effluent from the water condensation unit of the ODH configuration is first fed to a carbon dioxide removal unit as part of the ODH configuration wherein carbon dioxide is removed by an aqueous solution of an amine, and then fed to the carbon dioxide removal unit of the steam cracker configuration wherein carbon dioxide is removed by an aqueous solution of sodium hydroxide. Such set-up can be applied in the process depicted in FIG. 2.

The present integrated process is inter alia characterized in that it comprises a step (hereinafter also referred to as "oxidation step") of removing unconverted oxygen, carbon monoxide and acetylene from at least a portion of the stream coming from the ODH unit by oxidation of carbon monoxide and acetylene into carbon dioxide in an oxidation unit which is located at a position (a) which is downstream of the ODH unit, preferably downstream of the water condensation unit of the ODH configuration, and (b) which is downstream of the steam cracker unit, preferably downstream of the water condensation unit of the steam cracker configuration, and upstream of the carbon dioxide removal unit of the steam cracker configuration.

In the above-mentioned oxidation step, oxygen may be added, that is to say in addition to unconverted oxygen originating from the ODH unit that is still present in the feed to the oxidation step.

Further, in said oxidation step, the temperature may vary within wide ranges and is generally of from 50 to 500° C., for example of from 100 to 400° C. Preferably, in said oxidation step, the temperature is in the range of from 100 to 400° C., more preferably 150 to 300° C., most preferably 200 to 260° C. Still further, in said oxidation step, typical pressures are 0.1-30 or 0.1-20 bara (i.e. "bar absolute"). Further, preferably, said pressure is of from 0.1 to 15 bara, more preferably of from 1 to 8 bara, most preferably of from 2 to 7 bara.

Suitably, the stream resulting from said oxidation step comprises no oxygen or a residual amount of oxygen which is at most 10,000 parts per million by volume (ppmv) or at most 1,000 ppmv or at most 500 ppmv or at most 100 ppmv or at most 50 ppmv or at most 10 ppmv or at most 2 ppmv or at most 1 ppmv, based on the total volume of the stream resulting from said oxidation step. Further, suitably, in said oxidation step, carbon monoxide and acetylene may be removed to such an extent that the stream resulting from said oxidation step comprises no carbon monoxide and acetylene or a residual amount of carbon monoxide and acetylene which is at most 15 vol. % or at most 10 vol. % or at most 5 vol. % or at most 1 vol. % or at most 500 parts per million by volume (ppmv) or at most 100 ppmv or at most 50 ppmv or at most 10 ppmv or at most 2 ppmv or at most 1 ppmv, based on the total volume of the stream resulting from said oxidation step.

Said oxidation step may be carried out in the presence of an oxidation catalyst. Suitably, said oxidation catalyst catalyzes the conversion of carbon monoxide, acetylene and oxygen into carbon dioxide by means of oxidation of carbon monoxide and acetylene into carbon dioxide.

Preferably, the oxidation catalyst that may be used in said oxidation step comprises a transition metal. More preferably, said catalyst comprises one or more metals selected from the group consisting of nickel (Ni), copper (Cu), zinc (Zn), palladium (Pd), silver (Ag), platinum (Pt), gold (Au), iron (Fe), manganese (Mn), cerium (Ce), tin (Sn), ruthenium (Ru) and chromium (Cr), more preferably one or more metals selected from the group consisting of nickel, copper, zinc, silver, platinum and ruthenium, more preferably one or more metals selected from the group consisting of nickel, copper, zinc, platinum and ruthenium, more preferably one or more metals selected from the group consisting of nickel, copper, zinc and silver, even more preferably one or more metals selected from the group consisting of nickel, copper and zinc. Most preferably, said catalyst comprises copper and/or platinum. Suitably, said catalyst comprises copper or platinum, more suitably copper. For example, said catalyst may comprise copper and zinc. In particular, said catalyst may be a metal oxide catalyst, which may be a partially reduced metal oxide catalyst, wherein the metal(s) is (are) as described above, for example a catalyst comprising copper oxide and optionally zinc oxide. The catalyst may be a supported catalyst, wherein one or more of said metals are carried by a support, or an unsupported catalyst. In case the catalyst is a supported catalyst, the support may be any support, for example alumina, titania, silica, zirconia or silicon carbide, suitably alumina. Further, the supported catalyst may be shaped into any shape, including tablets and extrudates, or coated on a substrate.

Further, the above-mentioned oxidation catalyst that may be used in said oxidation step may comprise one or more metals selected from the group consisting of palladium, silver, platinum, gold, copper and ruthenium, or one or more metals selected from the group consisting of palladium, silver, platinum and gold, or platinum.

In the process of the present invention, each unit may comprise one or more feed lines and one or more effluent lines, and an effluent line of a unit of the ODH configuration may be integrated with a feed line or effluent line of a unit of the steam cracker configuration. Within the present specification, "integration" of a line from the ODH configuration with a line from the steam cracker configuration means that the two lines in question are connected.

In the process of the present invention, the effluent line of a unit of the ODH configuration that may be integrated with a feed line or effluent line of a unit of the steam cracker configuration, may be one or more of the following: a) an effluent line of the water condensation unit; b) an effluent line of the optional carbon dioxide removal unit; c) an effluent line of the optional drying unit; and d) an effluent line of the oxidation unit if the oxidation unit is part of the ODH configuration.

Preferably, no feed line of the ODH unit is integrated with a feed line or effluent line of a unit of the steam cracker configuration, with the exception that a feed line of the steam cracker unit and a feed line of the ODH unit may be integrated, and/or that an optional recycle effluent line of the C2 separation unit and a feed line of the ODH unit may be integrated.

The process of the present invention is further illustrated by FIGS. 1-3.

In FIG. 1, a steam cracker configuration is shown. Said steam cracker configuration comprises steam cracker unit 2, water condensation unit 3b, carbon dioxide removal unit 4, drying unit 8, separation units 11, 15, 19 and 24 and optional acetylene hydrogenation unit 22. All of said separation units 11, 15, 19 and 24 are distillation columns. Further, in FIG. 1, an oxidative dehydrogenation (ODH) configuration integrated with said steam cracker configuration is also shown. Said ODH configuration comprises ODH unit 31 and water condensation unit 33.

Stream 1 comprising saturated hydrocarbons (e.g. ethane or naphtha) is fed to steam cracker unit 2 operating under steam cracking conditions. Product stream 3a coming from steam cracker unit 2 comprises water, C3+ hydrocarbons, ethane, ethylene, acetylene, methane, hydrogen, carbon monoxide and carbon dioxide. Said stream 3a is fed to water condensation unit 3b. In water condensation unit 3b, water and a portion of the C3+ hydrocarbons (in particular those C3+ hydrocarbons having a relatively high molecular weight) are removed by condensation via stream 3c. At least a portion of said stream 3c, comprising C3+ hydrocarbons, ethane, ethylene, acetylene, methane, hydrogen, carbon monoxide and carbon dioxide, is fed to carbon dioxide removal unit 4. Carbon dioxide removal agent is fed to carbon dioxide removal unit 4 via stream 5. Said carbon dioxide removal agent may be an aqueous solution of a base, for example sodium hydroxide or an amine. Carbon dioxide removal unit 4 may comprise a subunit wherein carbon dioxide is removed by an aqueous solution of an amine and a downstream subunit wherein carbon dioxide is removed by an aqueous solution of sodium hydroxide. Carbon dioxide is removed via aqueous stream 6.

Stream 28 comprising ethane and stream 30 comprising an oxidizing agent are fed to ODH unit 31 containing an ODH catalyst and operating under ODH conditions. In case ethane is fed to steam cracker unit 2, the source of ethane as fed to steam cracker unit 2 and ODH unit 31 may be the same or different. In a case where the source is the same, ethane from stream 1 may be fed via stream 29 and stream 28 to ODH unit 31. Product stream 32 coming from ODH unit 28 comprises water, ethane, ethylene, unconverted oxygen, acetylene, carbon monoxide, carbon dioxide and any acetic acid. At least a portion of said stream 32 is fed to water condensation unit 33. In water condensation unit 33, water and any acetic acid are removed by condensation via stream 34. At least a portion of stream 35 coming from water condensation unit 33, is fed to carbon dioxide removal unit 4 which is part of the steam cracker configuration.

In the process of the present invention, there is an oxidation unit wherein unconverted oxygen originating from the ODH unit and carbon monoxide and acetylene are removed by oxidation of carbon monoxide and acetylene, using said unconverted oxygen, into carbon dioxide. In accordance with the present invention, the oxidation unit may be located at one of the following positions, as indicated in FIG. 1 by "(X)": a) in line 32; b) in line 35; c) in line 3c upstream of the point where lines 3c and 35 are integrated. In said cases a) and b), the oxidation unit is part of the ODH configuration, whereas in said case c) it is part of the steam cracker configuration. The stream coming from the oxidation unit does not comprise unconverted oxygen, carbon monoxide and/or acetylene, or comprises a reduced amount thereof. In said cases a) and b), stream 7 coming from carbon dioxide removal unit 4 comprises acetylene and carbon monoxide originating from steam cracker unit 2, whereas in said case c) said stream 7 does not comprise carbon monoxide and/or acetylene, or comprises a reduced amount thereof.

Thus, stream 7 coming from carbon dioxide removal unit 4 comprises C3+ hydrocarbons, ethane, ethylene, optionally acetylene, methane, hydrogen, optionally carbon monoxide, and water. Said stream 7 is fed to drying unit 8. In drying unit 8, water is removed via stream 9. Stream 10 coming from drying unit 8, which comprises C3+ hydrocarbons, ethane, ethylene, optionally acetylene, methane, hydrogen and optionally carbon monoxide, is fed to separation unit 11.

In a first embodiment, in separation unit 11, said stream 10 is separated into a top stream 12 comprising methane, hydrogen and optionally carbon monoxide and a bottom stream 13 comprising C3+ hydrocarbons, ethane, ethylene and optionally acetylene. In said first embodiment, stream 13 is fed as stream 14 to separation unit 15. In separation unit 15, stream 14 is separated into a top stream 17 comprising ethane, ethylene and optionally acetylene and a bottom stream 16 comprising C3+ hydrocarbons.

In a second embodiment, in separation unit 11, said stream 10 is separated into a top stream 12 comprising ethane, ethylene, optionally acetylene, methane, hydrogen and optionally carbon monoxide and a bottom stream 13 comprising C3+ hydrocarbons. In said second embodiment, stream 12 is fed as stream 18 to separation unit 19. In separation unit 19, stream 12 is separated into a top stream 20 comprising methane, hydrogen and optionally carbon monoxide and a bottom stream 21 comprising ethane, ethylene and optionally acetylene.

Stream 17 comprising ethane, ethylene and optionally acetylene (above-mentioned first embodiment) or stream 21 comprising ethane, ethylene and optionally acetylene (above-mentioned second embodiment) is fed (i) to acetylene hydrogenation unit 22 in above-mentioned cases a) and b) wherein said streams 17 and 21 comprise acetylene (originating from steam cracker unit 2) or (ii) directly to separation unit 24 (a "C2 separation unit") in above-mentioned case c). In acetylene hydrogenation unit 22, acetylene is hydrogenated using hydrogen stream 22a into ethylene resulting in a stream 23 comprising ethane and ethylene. Said stream 23 is fed to separation unit 24. In separation unit 24, a stream comprising ethane and ethylene is separated into a top stream 25 comprising ethylene and a bottom stream 26 comprising ethane. Ethane from stream 26 may be recycled via stream 27. Stream 27a coming from stream 27 and comprising ethane may be fed to steam cracker unit 2. Stream 27b coming from stream 27 and comprising ethane may be fed to ODH unit 31.

In FIG. 2, a steam cracker configuration and an oxidative dehydrogenation (ODH) configuration integrated with said steam cracker configuration are shown. The steam cracker configuration of FIG. 2 comprises the same units as the steam cracker configuration of FIG. 1 as described above. Further, the ODH configuration of FIG. 2 comprises the same units as the ODH configuration of FIG. 1 as described above, and additionally comprises carbon dioxide removal unit 37.

The process of FIG. 2 is the same as the process of FIG. 1, with the exception that at least a portion of stream 35 coming from water condensation unit 33 which is part of the ODH configuration, is fed, via stream 36, to carbon dioxide removal unit 37 which is part of the ODH configuration. Carbon dioxide removal agent is fed to carbon dioxide removal unit 37 via stream 38. Said carbon dioxide removal agent may be an aqueous solution of a base, for example sodium hydroxide or an amine. Carbon dioxide is removed via aqueous stream 39. At least a portion of stream 40 coming from carbon dioxide removal unit 37, is fed to carbon dioxide removal unit 4 which is part of the steam cracker configuration. Carbon dioxide removal unit 37 may comprise a subunit wherein carbon dioxide is removed by an aqueous solution of an amine and a downstream subunit wherein carbon dioxide is removed by an aqueous solution of sodium hydroxide. Generally, the effluent from an ODH unit contains relatively more carbon dioxide than the effluent from a steam cracker unit. Therefore, alternatively, carbon dioxide removal unit 37 may only comprise a unit wherein carbon dioxide is removed by an aqueous solution of an amine, and further, carbon dioxide removal unit 4 may only comprise a unit wherein carbon dioxide is removed by an aqueous solution of sodium hydroxide.

In accordance with the present invention, also in the process of FIG. 2 an oxidation unit is used wherein unconverted oxygen originating from the ODH unit and carbon monoxide and acetylene are removed by oxidation of carbon monoxide and acetylene, using said unconverted oxygen, into carbon dioxide. Said oxidation unit may be located at one of the following positions, as indicated in FIG. 2 by "(X)": a) in line 32; b) in line 35 or 36; c) in line 40; d) in line 3c upstream of the point where lines 3c and 40 are integrated. In said cases a), b) and c), the oxidation unit is part of the ODH configuration, whereas in said case d) it is part of the steam cracker configuration. The stream coming from the oxidation unit does not comprise unconverted oxygen, carbon monoxide and/or acetylene, or comprises a reduced amount thereof. In said cases a), b) and c), stream 7 coming from carbon dioxide removal unit 4 comprises acetylene and carbon monoxide originating from steam cracker unit 2, whereas in said case d) said stream 7 does not comprise carbon monoxide and/or acetylene, or comprises a reduced amount thereof. Regarding said cases c) and d), the ratio of carbon dioxide produced in ODH unit 31 to carbon dioxide produced in the oxidation unit from feed coming from ODH unit 31 may be about 2:1, so that it is advantageous in said cases c) and d) that a relatively large portion of carbon dioxide is first removed in carbon dioxide removal unit 37 in the ODH configuration whereas the additional carbon dioxide produced in the oxidation unit can then still be removed in carbon dioxide removal unit 4 in the steam cracker configuration.

In FIG. 3, a steam cracker configuration and an oxidative dehydrogenation (ODH) configuration integrated with said steam cracker configuration are shown. The steam cracker configuration of FIG. 3 comprises the same units as the steam cracker configuration of FIG. 2 as described above. Further, the ODH configuration of FIG. 3 comprises the same units as the ODH configuration of FIG. 2 as described above, and additionally comprises drying unit 42.

The process of FIG. 3 is the same as the process of FIG. 2, with the exception that stream 40 coming from carbon dioxide removal unit 37 which is part of the ODH configuration, is fed, via stream 41, to drying unit 42 which is part of the ODH configuration. In drying unit 42, water is removed via stream 43. In a first embodiment of FIG. 3, which corresponds to the first embodiment as described with respect to FIG. 1, stream 44 is sent as stream 45 to separation unit 11 which is part of the steam cracker configuration. In a second embodiment of FIG. 3, which corresponds to the second embodiment as described with respect to FIG. 1, stream 44 is sent as stream 46 to separation unit 19 which is part of the steam cracker configuration.

In accordance with the present invention, also in the process of FIG. 3 an oxidation unit is used wherein unconverted oxygen originating from the ODH unit and carbon monoxide and acetylene are removed by oxidation of carbon monoxide and acetylene, using said unconverted oxygen, into carbon dioxide. Said oxidation unit may be located at one of the following positions, as indicated in FIG. 3 by "(X)": a) in line 32; b) in line 35 or 36. In said cases a) and b), the oxidation unit is part of the ODH configuration. The stream coming from the oxidation unit does not comprise unconverted oxygen, carbon monoxide and/or acetylene, or comprises a reduced amount thereof. In said cases a) and b), stream 7 coming from carbon dioxide removal unit 4 comprises acetylene and carbon monoxide originating from steam cracker unit 2.

Further, in FIGS. 1-3, acetylene hydrogenation unit 22 may be placed at another position within the steam cracker configuration. In FIGS. 1 and 2, acetylene hydrogenation unit 22 may be placed at any one of the following positions (not shown in FIGS. 1 and 2): 1) between drying unit 8 and separation unit 11; 2) between separation units 11 and 19 (in second embodiment as described with respect to FIG. 1); 3) between separation units 11 and 15 (in first embodiment as described with respect to FIG. 1). In FIG. 3, acetylene hydrogenation unit 22 may be placed at any one of the following positions (not shown in FIG. 3): 1) between separation unit 11 and the point at which streams 10 and 45 are combined (in first embodiment as described with respect to FIG. 1); 2) between separation unit 19 and the point at which streams 18 and 46 are combined (in second embodiment as described with respect to FIG. 1); 3) between separation units 11 and 15 (in first embodiment as described with respect to FIG. 1). In all of these cases, if hydrogen originating from steam cracker unit 2 is still present, advantageously no separate hydrogen stream 22a needs to be fed to acetylene hydrogenation unit 22.

In a further embodiment (not shown in FIGS. 1-3), a feed comprising fresh ethane and optionally propane is introduced into the downstream section of the steam cracker configuration, in particular into line 10 to column 11 or into line 14 to column 15, by which any propane from the fresh ethane feed is advantageously removed together with any C3+ hydrocarbons originating from the steam cracker unit, thereby removing the need to use a separate, additional depropanizer. In said further embodiment, fresh ethane does not have to be fed directly to ODH reactor 31, but an ethane recycle from line 27 can be sufficient. Said ethane recycle from line 27 would still comprise fresh ethane, that is to say the fresh ethane as fed to column 11 or 15, which ethane was not subjected to steam cracking conditions and neither to oxidative dehydrogenation (ODH) conditions. Thus, fresh ethane as fed in the foregoing way (that is to say, indirectly via line 10 or line 14) to the ODH unit would thus originate from a source other than a source of fresh ethane that may be used to feed ethane directly to the steam cracker unit. In addition, said ethane recycle from line 27 would comprise unconverted ethane, that is to say unconverted ethane originating from the steam cracker unit.

We claim:

1. Process for the production of ethylene in an integrated configuration comprising a steam cracker configuration and an oxidative dehydrogenation (ODH) configuration, wherein the steam cracker configuration comprises a steam cracker unit, a water condensation unit and a carbon dioxide removal unit and the ODH configuration comprises an ODH unit and a water condensation unit, which process comprises the following steps:
    subjecting a stream comprising saturated hydrocarbons to steam cracking conditions in the steam cracker unit, resulting in a stream comprising water, unconverted ethane, ethylene, acetylene, hydrogen, methane, carbon monoxide, carbon dioxide and C3+ hydrocarbons;
    feeding at least a portion of the stream coming from the steam cracker unit to the water condensation unit of the steam cracker configuration, and removing water and a portion of the C3+ hydrocarbons from said stream by condensation in the water condensation unit, resulting in a stream comprising unconverted ethane, ethylene, acetylene, hydrogen, methane, carbon monoxide, carbon dioxide and C3+ hydrocarbons;
    subjecting a stream comprising ethane and oxygen to oxidative dehydrogenation (ODH) conditions in the ODH unit, resulting in a stream comprising unconverted ethane, ethylene, acetylene, unconverted oxygen, water, carbon monoxide and carbon dioxide;
    feeding at least a portion of the stream coming from the ODH unit to the water condensation unit of the ODH configuration, and removing water from said stream by condensation in the water condensation unit, resulting in a stream comprising unconverted ethane, ethylene, acetylene, unconverted oxygen, carbon monoxide and carbon dioxide;
    feeding an effluent coming from the ODH configuration, which effluent comprises unconverted ethane and ethylene, to the steam cracker configuration at a position which is downstream of the steam cracker unit;
    removing unconverted oxygen, carbon monoxide and acetylene from at least a portion of the stream coming from the ODH unit by oxidation of carbon monoxide and acetylene into carbon dioxide in an oxidation unit which is located at a position (a) which is downstream of the ODH unit, and (b) which is downstream of the steam cracker unit, and upstream of the carbon dioxide removal unit of the steam cracker configuration;
    feeding a stream comprising unconverted ethane, ethylene, optionally acetylene, hydrogen, methane, optionally carbon monoxide, carbon dioxide and C3+ hydrocarbons to the carbon dioxide removal unit of the steam cracker configuration, and removing carbon dioxide from said stream in the carbon dioxide removal unit of the steam cracker configuration, resulting in a stream comprising unconverted ethane, ethylene, optionally acetylene, hydrogen, methane, optionally carbon monoxide and C3+ hydrocarbons; and
    recovering unconverted ethane and ethylene from at least a portion of the stream coming from the carbon dioxide removal unit of the steam cracker configuration and optionally from at least a portion of the effluent coming from the ODH configuration, which effluent comprises unconverted ethane and ethylene, which is fed to the steam cracker configuration at a position which is downstream of the carbon dioxide removal unit of the steam cracker configuration.

2. The process according to claim 1, wherein the oxidation unit is part of the steam cracker configuration and is located at a position (a) which is downstream of the position at which the effluent coming from the ODH configuration, which effluent comprises unconverted ethane and ethylene, is fed to the steam cracker configuration, wherein said effluent additionally comprises acetylene, unconverted oxygen, carbon monoxide and optionally carbon dioxide, and (b) which is upstream of the carbon dioxide removal unit of the steam cracker configuration.

3. The process according to claim 1, wherein the oxidation unit is part of the ODH configuration and is located at a position (a) which is upstream or downstream, and (b) which is upstream or downstream, of an optional carbon dioxide removal unit of the ODH configuration, and (c) which is upstream of the position at which the effluent coming from the ODH configuration, which effluent comprises unconverted ethane and ethylene, is fed to the steam cracker configuration, wherein said effluent additionally comprises optionally carbon dioxide.

4. The process according to claim 1, wherein saturated hydrocarbons are fed to the steam cracker unit which comprise one or more of ethane, propane, butane, liquefied petroleum gas (LPG), naphtha, hydrowax and recycled waste plastics oil.

5. The process according to claim 1, wherein ethane is fed to the ODH unit which originates from one or more sources selected from the group consisting of a) a source of fresh ethane that is used to feed ethane to the steam cracker unit; b) another source of fresh ethane, other than said first source mentioned under a); and c) unconverted ethane as recovered in the process according to claim 1.

6. The process according to claim 1, wherein the steam cracker configuration additionally comprises a $1^{st}$ separation unit, and the effluent coming from the ODH configuration, which effluent comprises unconverted ethane and ethylene, is fed to the steam cracker configuration at a position which is upstream of the $1^{st}$ separation unit, and the process additionally comprises the following steps:
    feeding at least a portion of the stream coming from the carbon dioxide removal unit of the steam cracker configuration and optionally at least a portion of the effluent coming from the ODH configuration, which effluent comprises unconverted ethane and ethylene, which is fed to the steam cracker configuration at a position which is downstream of the carbon dioxide removal unit of the steam cracker configuration, to the $1^{st}$ separation unit; and separating said stream or streams in the $1^{st}$ separation unit into a stream comprising hydrogen, methane and optionally carbon monoxide and a stream comprising C3+ hydrocarbons.

7. The process according to claim 6, wherein the steam cracker configuration additionally comprises a C2 separation unit, and the process additionally comprises the following steps:
- feeding unconverted ethane and ethylene from a stream comprising unconverted ethane, ethylene, optionally acetylene, hydrogen, methane, optionally carbon monoxide and C3+ hydrocarbons to the C2 separation unit; and
- separating said stream in the C2 separation unit into a stream comprising ethylene and a stream comprising unconverted ethane;

wherein:
- unconverted ethane and ethylene from the stream comprising unconverted ethane and ethylene coming from the water condensation unit of the ODH configuration are fed to the C2 separation unit.

8. The process according to claim 7, wherein the steam cracker configuration additionally comprises a $2^{nd}$ separation unit, and the process additionally comprises the following steps:
1) In a first embodiment:
- separating a stream comprising unconverted ethane, ethylene, optionally acetylene, hydrogen, methane, optionally carbon monoxide and C3+ hydrocarbons in the $1^{st}$ separation unit into a stream comprising hydrogen, methane and optionally carbon monoxide and a stream comprising C2+ hydrocarbons, which C2+ hydrocarbons comprise unconverted ethane, ethylene, optionally acetylene and C3+ hydrocarbons;
- feeding at least a portion of the separated stream comprising C2+ hydrocarbons coming from the $1^{st}$ separation unit to the $2^{nd}$ separation unit wherein said stream is separated into a stream comprising C2 hydrocarbons, which C2 hydrocarbons comprise unconverted ethane, ethylene and optionally acetylene, and a stream comprising C3+ hydrocarbons; and
- feeding unconverted ethane and ethylene from the separated stream comprising C2 hydrocarbons coming from the $2^{nd}$ separation unit to the C2 separation unit wherein they are separated into a stream comprising ethylene and a stream comprising unconverted ethane; or 2) In a second embodiment:
- separating a stream comprising unconverted ethane, ethylene, optionally acetylene, hydrogen, methane, optionally carbon monoxide and C3+ hydrocarbons in the $1^{st}$ separation unit into a stream comprising hydrogen, methane, optionally carbon monoxide and C2 hydrocarbons, which C2 hydrocarbons comprise unconverted ethane, ethylene and optionally acetylene, and a stream comprising C3+ hydrocarbons;
- feeding at least a portion of the separated stream comprising hydrogen, methane, optionally carbon monoxide and C2 hydrocarbons coming from the $1^{st}$ separation unit to a $2^{nd}$ separation unit wherein said stream is separated into a stream comprising hydrogen, methane and optionally carbon monoxide and a stream comprising C2 hydrocarbons; and
- feeding unconverted ethane and ethylene from the separated stream comprising C2 hydrocarbons coming from the $2^{nd}$ separation unit to the C2 separation unit wherein they are separated into a stream comprising ethylene and a stream comprising unconverted ethane.

9. The process according to claim 1, wherein the stream coming from the carbon dioxide removal unit of the steam cracker configuration comprises acetylene, and the steam cracker configuration additionally comprises an acetylene removal unit, and the process additionally comprises the following step:
- an acetylene removal step wherein in the acetylene removal unit acetylene is removed from a stream comprising acetylene, ethylene and optionally unconverted ethane.

* * * * *